United States Patent
Hikida et al.

(10) Patent No.: US 6,645,936 B1
(45) Date of Patent: *Nov. 11, 2003

(54) REDUCING POSTOPERATIVE ASTIGMATISM

(75) Inventors: Mitsushi Hikida, Ikoma (JP); Masaaki Hayashi, Ikoma (JP)

(73) Assignee: Santen Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 865 days.

(21) Appl. No.: 08/945,901

(22) PCT Filed: Apr. 23, 1996

(86) PCT No.: PCT/JP96/01092

§ 371 (c)(1),
(2), (4) Date: Nov. 4, 1997

(87) PCT Pub. No.: WO96/35448

PCT Pub. Date: Nov. 14, 1996

(30) Foreign Application Priority Data

May 8, 1995 (JP) .............................................. 7-109239

(51) Int. Cl.⁷ .......................... A61K 38/00; A61K 38/16
(52) U.S. Cl. ........................................... 514/12; 514/21
(58) Field of Search ....................... 514/12, 2

(56) References Cited

U.S. PATENT DOCUMENTS 5,561,109 A * 10/1996 Mita et al. .................... 514/12

FOREIGN PATENT DOCUMENTS

| JP | 2-48534 | 2/1990 |
| JP | 8-40925 | 2/1996 |
| WO | WO 92/08477 | 5/1992 |

OTHER PUBLICATIONS

Database BIOSIS AN 85:168487. Jensen O.L. et al. In: Peeters, H. (ED.). Protides of the Biological Fluids; Proceedings of the Colloquium, vol. 32. Immunoglobulins, Tumor Markers and Targeting Adances in Separation of Protides; Brussels, Belgium, 19, Jan. 1985.*

Hirasaka, T., Namiki, M., Katakami, C., Yamamoto, M., "Corneoslceral Wound Healing after Self–sealing Cataract Surgery", *Journal of Japanese Ophthalmological Society,* 98, 636–640 (1994).

Momose, A., "Stepped Penetrating Keratoplasty—A New Technique to Reduce Postoperative Corneal Astigmatism", *Japanese Journal of Ophthalmic Surgery,* 6, 319–323 (1993).

Sakka, Y., Shimokawa, S., "Human Fibrin Seal for Limbal Wound Closure after KPE", *Journal of the Eye,* 4, 250–252 (1987).

* cited by examiner

*Primary Examiner*—Michael Borin
(74) *Attorney, Agent, or Firm*—Frishauf, Holtz, Goodman & Chick, P.C.

(57) ABSTRACT

An object of the present invention is to find a drug which is useful for prevention of postoperative astigmatism. The present invention provides a preventive for postoperative astigmatism which comprises lactoferrin as an active ingredient. A preferred dosage form of the preventive for postoperative astigmatism is an ophthalmic solution, and a preferred concentration of lactoferrin is 0.1 to 1.0% (w/v).

18 Claims, No Drawings

REDUCING POSTOPERATIVE ASTIGMATISM

TECHNICAL FIELD

The present invention relates to a preventive for postoperative astigmatism which comprises lactoferrin as an active ingredient.

BACKGROUND ART

Surgical techniques which are safe and hardly cause inflamation have been established in recent cataract surgery and corneal transplantation. A problem of surgeons is to suppress postoperative disorders. One of serious postoperative disorders is astigmatism caused by distortions of a wound closure site, so-called postoperative astigmatism.

Various attempts have hitherto been made in order to reduce postoperative astigmatism. For example, in cataract surgery, postoperative astigmatism can be reduced by incising sclera and cornea simultaneously (hereinafter referred to as sclerocorneal incision), and injecting an intraocular irrigating solution after phacoemulsification to self-close the wound. This method has also an effect that infiltration of inflammatory cells caused by sutures is not observed in an early period after surgery since no suture is used (Journal of Japanese Ophthalmological Society, 9, 636–640 (1994)). In addition, it is reported that early suture removal is possible and postoperative astigmatism is reduced by trephining host cornea in two stages in penetrating keratoplasty (Japanese Journal of Ophthalmic Surgery, 6, 319–323 (1993)). These reports relate to methods of preventing postoperative astigmatism mainly by improvement of the surgical procedures. On the other hand, as an example of using drugs, it is reported that astigmatism, which is observed just after surgery, is reduced by using a bioadhesive such as fibrin glue after sclerocorneal suture in cataract surgery and removing a suture in an early stage (Journal of the Eye, 4, 250–252 (1987)). However, this method has some problems. For example, if the bioadhesive administered from the outside comes into contact with iris, the bioadhesive may adhere to the iris and cause inflammation.

On the other hand, lactoferrin is a protein existing in milk and tears of human being, bovine, etc. and is known to have pharmacological effects such as an antibacterial effect and a lymphocyte proliferation effect (Japanese Laid-open Patent Publication No. 48534/1990). In addition, it is recognized that lactoferrin has an excellent effect on promoting corneal keratocyte proliferation and is useful as a therapeutic agent for corneal disorders in the ophthalmic field (WO 92/08477).

However, no study has been made on use of lactoferrin for ophthalmic surgery, in particular, use of lactoferrin for cataract surgery and corneal transplantation intending to prevent postoperative astigmatism.

It was a very interesting subject to find a drug which is useful for preventing postoperative astigmatism, which is particularly serious among the postoperative disorders in cataract surgery and corneal transplantation.

The distortion of the wound closure site after sclerocorneal incision or corneal incision is considered to be a cause of postoperative astigmatism. If the wound closure strength is weak, a slippage of the closure or unevenness on the corneal surface is caused by a change in intraocular pressure, etc., and thereby causing the distortion of the wound closure site.

Seeking for drugs which increase the strength of the wound closure site in order to find a new preventive for postoperative astigmatism, the inventors found out lactoferrin increases the wound closure strength after corneal incision. Namely, lactoferrin was proved to be useful as the preventive for postoperative astigmatism.

DISCLOSURE OF THE INVENTION

The present invention relates to a preventive for postoperative astigmatism which comprises lactoferrin as an active ingredient.

"Postoperative astigmatism" in the present invention stands for astigmatism caused by distortions of a wound closure site due to weak wound closure strength after sclerocorneal incision or corneal incision in cataract surgery, penetrating keratoplasty, etc.

Various attempts have hitherto been made in order to reduce postoperative astigmatism in cataract surgery and corneal transplantation (Journal of the Eye, 4, 250–252 (1987), Japanese Journal of Ophthalmic Surgery, 6, 319–323 (1993) and Journal of Japanese Ophthalmological Society, 98, 636–640 (1994)). Development of an ophthalmic solution which can furthermore reduce postoperative astigmatism is desired.

On the other hand, it is disclosed that lactoferrin has an antibacterial effect, a lymphocyte proliferation effect (Japanese Laid-open Patent Publication No. 48534/1990) and a keratocyte proliferation promotion effect (WO 92/08477). However, there has not been reported yet use of lactoferrin in cataract surgery and corneal transplantation intending to prevent postoperative astigmatism.

The inventors sought for drugs which increase the strength of the wound closure site in order to find a preventive for postoperative astigmatism. As a result, as detailed data will be shown in the item of effects of the invention, lactoferrin was found to increase the strength of the wound closure site after corneal incision and was proved to be useful as the preventive for postoperative astigmatism.

Examples of dosage forms of lactoferrin are an ophthalmic solution, injection, etc. Lactoferrin can be formulated into preparations by the conventional methods. For example, ophthalmic solutions can be prepared using isotonic agents such as sodium chloride and concentrated glycerin, buffering agents such as sodium phosphate and sodium acetate, non-ionic surfactants such as polyoxyethylene sorbitan monooleate (hereinafter referred to as "polysorbate"), stearic polyoxyl 40 and polyoxyethylene hydrogenated castor oil, stabilizing agents such as sodium citrate and sodium edetate, preservatives such as benzalkonium chloride and paraben, etc. The pH of the ophthalmic solutions can be in a range which is acceptable to ophthalmic preparations. A preferred pH range is 4 to 8.

The dosage can suitably be adjusted depending on symptoms, age, dosage form, etc. In the case of the ophthalmic solutions, the dosage is 0.01 to 3.0% (w/v), preferably 0.1 to 1.0% (w/v), and one to several drops can be instilled per day. In the case of injections, the usual daily dosage is 0.01 to 100 mg, preferably 0.1 to 10 mg, which can be given in one or a few divided doses.

The following examples for formulating the preparations of the lactoferrin ophthalmic solution are for better understanding of the present invention but do not limit the scope thereof.

BEST MODE FOR CARRYING OUT THE INVENTION

Preparation Example

Lactoferrin ophthalmic solutions having a lactoferrin concentration of 0.5% (w/v) (Formulation 1 to 6) were prepared so that the concentrations of the other ingredients than lactoferrin might come to those shown in Table 1.

The figures for each ingredient shown in Table 1 are expressed as % by weight (w/v).

TABLE 1

|  | Formulation 1 | Formulation 2 | Formulation 3 | Formulation 4 | Formulation 5 | Formulation 6 |
|---|---|---|---|---|---|---|
| Conc. glycerin | 2.5 | 2.5 | 2.5 | 2.48 | 2.33 | 2.33 |
| Sodium chloride | — | — | — | 0.006 | 0.06 | 0.06 |
| Polysorbate 80 | — | 0.001 | 0.001 | 0.01 | 0.001 | 0.01 |
| Benzalkonium chloride | — | — | 0.005 | 0.005 | 0.005 | 0.005 |

In addition, lactoferrin ophthalmic solutions having lactoferrin concentrations of 0.01, 0.1, 1.0 and 3.0% (w/v) were also prepared by changing the amount of lactoferrin to be added in each Formulation.

Pharmacological Test

Henrick et al. reported that wound closure strength can be evaluated by determining intraocular pressure after corneal incision (J. Cataract Refract. Surg., 13, 551–553 (1987)). Effects of lactoferrin on the wound closure strength were studied using rabbits by the following method according to the method described in this literature.

Experimental Method

In male Japanese white rabbits, corneal incisions 3.5-mm long were made, and lactoferrin was instilled four times per day since two hours after the surgery. The rabbits were sacrificed by anaesthesia five days after the surgery. A 25-gauge hypodermic needle connected with a pressure recorder and an injection pump was inserted into anterior chamber through cornea. Physiological saline was injected at a rate of 0.35 ml per minute, and changes in intraocular pressure were recorded.

The wound closure strength was shown by intraocular pressure at which a closure site leaks (hereinafter referred to as maximum intraocular pressure resistant to leak).

Results

Table 2 shows maximum intraocular pressure resistant to leak when 0, 0.01, 0.1 and 1.0% (w/v) lactoferrin ophthalmic solutions were instilled, as examples of experimental results.

TABLE 2

| Concentration of lactoferrin [% (w/v)] | Maximum intraocular pressure resistant to leak [mmHg] |
|---|---|
| 0 | 614.3 |
| 0.01 | 618.3 |
| 0.1 | 816.6 |
| 1.0 | 704.4 |

As shown in Table 2, the maximum intraocular pressure resistant to leak was raised by the instillation of lactoferrin, and the action of lactoferrin reached a plateau at a concentration of 0.1% (w/v).

From the above-mentioned results, it was recognized that lactoferrin has an excellent action on increasing the wound closure strength and is useful as a preventive for postoperative astigmatism.

INDUSTRIAL APPLICABILITY

The present invention relates to a preventive for postoperative astigmatism which comprises lactoferrin as an active ingredient.

What is claimed is:

1. A method for reducing postoperative astigmatism by increasing the strength of a wound closure site comprising administering to the eyes of a patient after sclerocorneal incision or corneal incision, a pharmaceutically effective amount of lactoferrin in a concentration of 0.1 to 1.0% (w/v) to reduce postoperative astigmatism.

2. The method of claim 1, wherein the lactoferrin is in the form of an ophthalmic solution.

3. The method of claim 1, wherein the lactoferrin is in the form of an ophthalmic solution and has a pH of 4 to 8.

4. The method of claim 3, wherein the ophthalmic solution comprises at least one of an isotonic agent, a buffering agent, a non-ionic surfactant, a stabilizing agent and a preservative.

5. The method of claim 3, wherein the ophthalmic solution comprises an isotonic agent selected from the group consisting of sodium chloride and concentrated glycerin.

6. The method of claim 5, wherein the opthalmic solution comprises a buffering agent selected from the group consisting of sodium phoshpate and sodium acetate.

7. The method of claim 6, wherein the ophthalmic solution comprises a non-ionic surfactant selected from the group consisting of polyoxyethylene sorbitan monooleate, stearic polyoxyl 40 and polyoxyethylene hydrogenated castor oil.

8. The method of claim 7, wherein the ophthalmic solution comprises a stabilizing agent selected from the group consisting of sodium citrate and sodium edetate.

9. The method of claim 8, wherein the ophthalmic solution comprises a preservative selected from the group consisting of benzalkonium chloride and paraben.

10. The method of claim 3, wherein the opthalmic solution comprises a concentrated glycerin, sodium chloride, polyoxyethylene sorbitan monooleate and benzalkonium chloride.

11. A method for reducing postoperative astigmatism by increasing the strength of a wound closure site comprising administering to the eyes of a patient that has undergone cataract surgery a pharmaceutically effective amount of lactoferrin in a concentration of 0.1 to 1.0% (w/v) to reduce postoperative astigmatism.

12. A method for reducing postoperative astigmatism by increasing the strength of a wound closure site comprising administering to the eyes of a patient that has undergone corneal transplantation a pharmaceutically effective amount of lactoferrin in a concentration of 0.1 to 1.0% (w/v) to reduce postoperative astigmatism.

13. The method of claim 11, wherein the lactoferrin is in the form of an ophthalmic solution and has a pH of 4 to 8.

14. The method of claim 13, wherein the ophthalmic solution comprises at least one of an isotonic agent selected from the group consisting of sodium chloride and concentrated glycerin; a buffering agent selected from the group consisting of sodium phosphate and sodium acetate; a non-ionic surfactant selected from the group consisting of polyoxyethylene sorbitan monooleate, stearic polyoxyl 40 and polyoxyethylene hydrogenated castor oil; a stabilizing agent selected from the group consisting of sodium citrate and sodium edetate; and a preservative selected from the group consisting of benzalkonium chloride and paraben.

15. The method of claim 13, wherein the ophthalmic solution comprises a concentrated glycerin, sodium chloride, polyoxyethylene sorbitan monooleate and benzalkonium chloride.

16. The method of claim 12, wherein the lactoferrin is in the form of an ophthalmic solution and has a pH of 4 to 8.

17. The method of claim 16, wherein the ophthalmic solution comprises at least one of an isotonic agent selected from the group consisting of sodium chloride and concentrated glycerin; a buffering agent selected from the group consisting of sodium phosphate and sodium acetate; a nonionic surfactant selected from the group consisting of polyoxyethylene sorbitan monooleate, stearic polyoxyl 40 and polyoxyethylene hydrogenated castor oil; a stabilizing agent selected from the group consisting of sodium citrate and sodium edetate; and a preservative selected from the group consisting of benzalkonium chloride and paraben.

18. The method of claim 16, wherein the ophthalmic solution comprises a concentrated glycerin, sodium chloride, polyoxyethylene sorbitan monooleate and benzalkonium chloride.

* * * * *